United States Patent [19]

Phipps, Sr. et al.

[11] Patent Number: 4,632,669
[45] Date of Patent: Dec. 30, 1986

[54] PRESSURE INDICATING MEDICAL INJECTION GUN

[75] Inventors: Cornelius M. Phipps, Sr., Glen Ellyn; Cornelius M. Phipps, Jr.; Hal A. Phipps, both of St. Charles, all of Ill.

[73] Assignee: Plastic Specialties, Inc., Glen Ellyn, Ill.

[21] Appl. No.: 607,967

[22] Filed: May 7, 1984

[51] Int. Cl.$^4$ .............................................. A61M 5/00
[52] U.S. Cl. ...................................... 604/118; 604/228
[58] Field of Search .................. 604/118, 121, 218, 223, 604/224, 227, 228

[56] References Cited

U.S. PATENT DOCUMENTS

| | | | |
|---|---|---|---|
| 2,567,895 | 9/1951 | Rommer | 604/121 |
| 2,735,431 | 2/1956 | Swanson | 604/223 |
| 2,742,901 | 4/1956 | Kranthamer | 604/121 |
| 2,892,457 | 6/1959 | Sturtz | 604/223 |
| 3,141,583 | 7/1964 | Mapel et al. | 604/223 |
| 3,517,668 | 6/1970 | Brickson | 604/223 |
| 4,022,207 | 5/1977 | Citrin | 604/218 |
| 4,231,715 | 11/1980 | Gleichner | 604/121 |

*Primary Examiner*—C. Fred Rosenbaum
*Assistant Examiner*—Gene B. Kartchner
*Attorney, Agent, or Firm*—Lee, Smith & Zickert

[57] ABSTRACT

A medical pressure indicating injection gun for injecting fluid into a balloon catheter, with a visual indication of the balloon pressure. The injection gun includes a barrel adapted for attachment thereto the body of a syringe, and a bracketed coupling shaft for holding the syringe plunger. The coupling shaft includes pressure gauge marks thereon, and is slideable within a cylinder chamber on the end of a ratchet shaft, and in compression with a spring also in the chamber. A ratchet mechanism is employed for engaging teeth on the ratchet shaft and advancing the ratchet shaft forward, and through the spring the coupling shaft and attached syringe plunger are advanced as well. Pressure build-up in the balloon catheter causes the coupling shaft to retract into the cylinder chamber in compression with the spring and indicate by the gauge marks the balloon pressure. A full length high leverage ratchet trigger operates the ratchet mechanism, and a ratchet release is operative to disengage the ratchet mechanism from the ratchet shaft. The ratchet shaft extends out of the rear of the gun and is used in conjunction with a pair of finger lugs on the gun frame to independently advance the ratchet shaft, much like a syringe.

13 Claims, 12 Drawing Figures

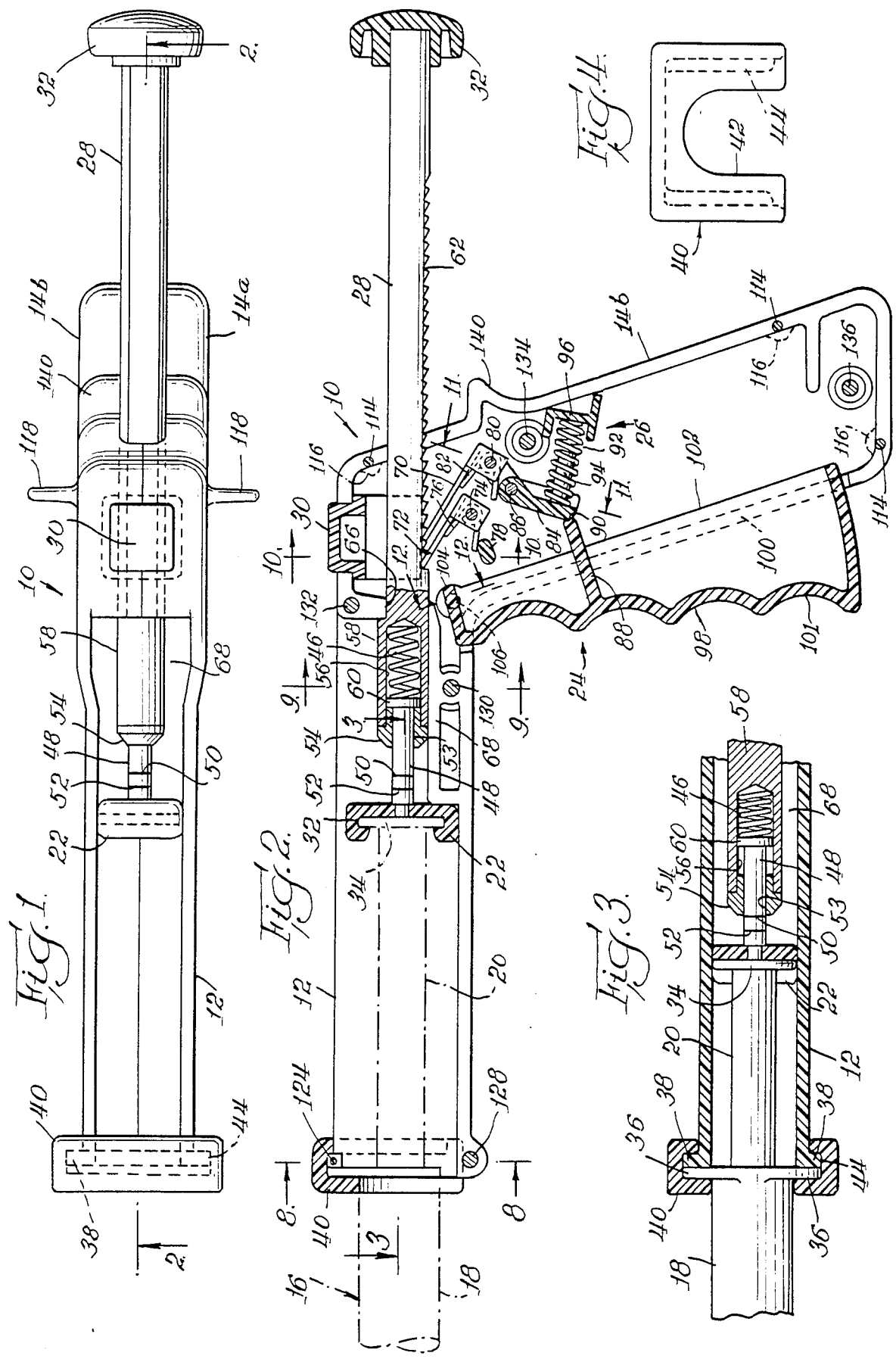

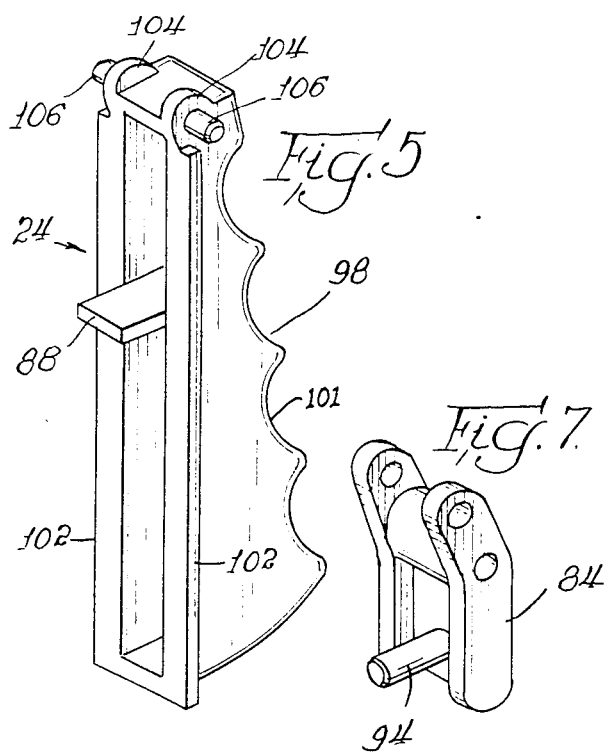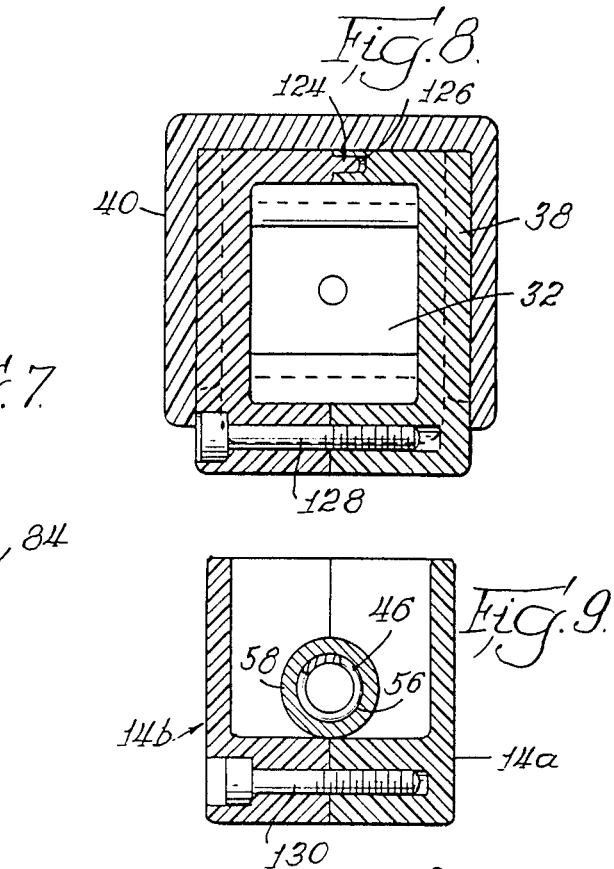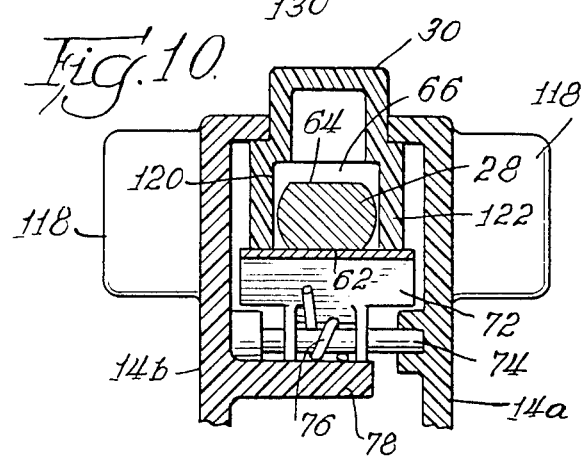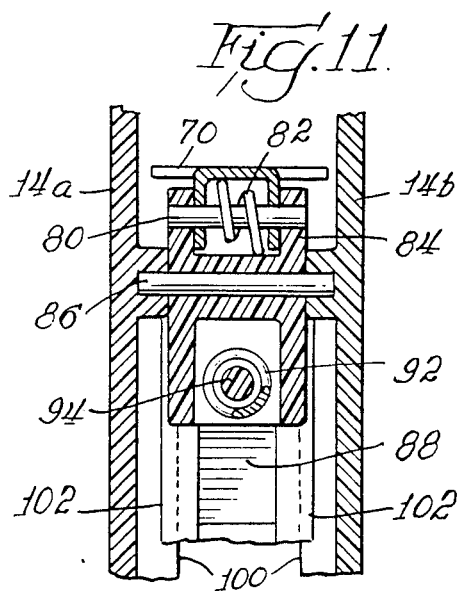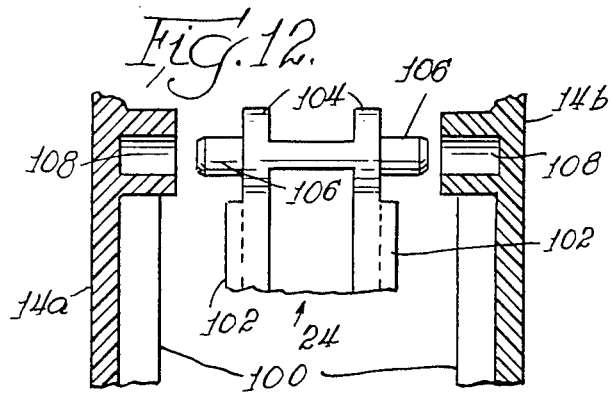

PRESSURE INDICATING MEDICAL INJECTION GUN

BACKGROUND OF THE INVENTION

The present invention relates in general to medical and surgical instruments, and more particularly to fluid injection or discharge devices.

The present invention has particular utility when used in connection with treating arteriosclerosis problems where an expandable balloon catheter is inserted into an artery and filled with a fluid to expand and collapse obstructing cholesterol deposits on the walls of arteries. It is a conventional practice to inject fluid into the balloon catheter through a connecting tube by a hypodermic syringe, or similar instrument. Other fluid injection devices are disclosed in U.S. Pat. Nos. 2,892,457 and 3,474,787.

the pressure that the balloon exerts on the artery walls is critical in compacting the desired amount of cholesterol deposits against the artery walls, and is directly proportional to the amount of fluid injected into the balloon catheter. The balloon pressure is also critical as excessive pressure may rupture the balloon or injure the delicate artery walls. The traditional practice of injecting fluid into such a type of caatheter with a conventional syringe instrument, as noted above, has met with varying degrees of success, when properly used.

One shortcoming of the use of the noted instruments is that the pressure buildup within the balloon catheter cannot be accurately gauged, except by noting the amount of fluid which has been discharged from the syringe. Because of various balloon catheter elasticities, the amount of fluid discharged from the syringe is not always proportional to the pressure which the balloon exerts on the artery walls. Although a fluroscope is of some help in visually locating the catheter at the proper position within the artery, it cannot accurately gauge the pressure exerted by the balloon catheter on the artery walls. The inadvertent injection of an excessive amount of fluid into the bulb can cause the balloon catheter to rupture.

Another shortcoming of hypodermic syringes in general, as well as the noted instruments in inflating balloon catheters is that such devices are not constructed to attain high balloon pressures, for example one hundred and fifty pounds per square inch.

There is therefore a need for a fluid injection device which indicates pertinent fluid pressures and thereby prevents an excessive amount of presure from developing, whereby the possibility of damaging artery walls or the expandable bulbs themselves is substantially reduced. It is thus the aim of the present invention to provide a medical fluid injection device with a pressure monitor which is ideally suited, but not restricted to the controlled injection of fluid into a balloon catheter.

There is also a need for an instrument which can be initially finger operated, much like a syringe, to quickly discharge fluids under low pressures, and subsequently hand operated to incrementally achieve greater fluid pressures.

Beacuse of advances in the treatment of arteriosclerosis, there is a demand for a high pressure injection gun which is operable with one hand.

SUMMARY OF THE INVENTION

The pressure indicating injection gun according to the present invention provides the capability of accurately inflating a balloon catheter with a liquid to a predetermined catheter pressure.

The invention is constructed generally in the form of a gun, or pistol with a barrel clip adapted for holding a conventional disposable hypodermic-type syringe. A trigger-operated ratchet assembly advances a ratchet shaft in a forward direction so as to push on the syringe plunger and discharge fluid into a balloon catheter. A coupling shaft connects the syringe plunger to the ratchet shaft by providing at one end thereof a slotted bracket for removable attachment to the syringe plunger rim, and at the other end the coupling shaft is slidable within a cylindrical chamber of the ratchet shaft. Disposed within the ratchet shaft chamber is a compression spring which acts to allow axial movement of the coupling shaft with respect to and into the ratchet shaft. The compression spring also includes a known compressibility such that when it is compressed a predetermined amount a desired pressure is known to exist in the balloon catheter.

The coupling shaft includes pressure indicating scale marks along its length to yield visual indications of increasing balloon pressures as the compression spring compresses and the coupling shaft slides into the ratchet shaft spring chamber. By noting the position of the coupling shaft scale marks with respect to the edge of the spring chamber the pressure within the balloon catheter can accurately be determined.

The barrel of the pressure pistol is contructed of a clear durable plastic so that the pressure marks can be readily seen through the sides or bottom of the barrel. The barrel also includes an open top so that the pressure indicating marks on the coupling shaft can be readily seen from the top of the instrument.

A full length hand trigger is pivotal at one end thereof and actuates a ratchet mechanism which engages teeth on the ratchet shaft so that the shaft can be advanced, and through the coupling shaft and compression spring, the syringe plunger is urged forwardly to force fluid into the balloon catheter. The ratchet trigger is of a length such that it can be grasped by all four fingers of the hand and squeezed to produce maximum force on the ratchet mechanism. Moreover, the trigger arm includes a ratchet mechanism actuating stub located on the trigger arm backside in a position corresponding to where the strongest fingers of one's hand are expected to grasp the trigger on the frontside. The stub is also located near the pivotal axis of the trigger to realize greater mechanical advantage of the lever arm. In this matter, the index and middle fingers, which are the strongest, can squeeze the trigger and apply maximum pressure on the ratchet mechanism.

The ratchet shaft end including a knob, extends rearwardly out of the pistol end, and with a pair of opposing finger lugs located on the sides of the pistol a person is able to initially advance the ratchet shaft with the thumb and fingers, much like a syringe. A ratchet release is located proximate the finger lugs for easy disengagement of the ratchet mechanism from the toothed ratchet shaft and thereby permit the ratchet shaft to either move rearwardly in response to catheter fluid pressure or be pushed forward freely.

BRIEF DESCRIPTION OF THE DRAWINGS

FIG. 1 is a top plan view of the medical pressure indicating pistol showing the open barrel for viewing the pressure scale, and the side mounted finger lugs.

FIG. 2 of the drawings is a sectional side view of the pressure indicating pistol taken along line 2—2 of FIG. 1.

FIG. 3 is a partial sectional view, taken along line 3—3 of FIG. 2, illustrating the pressure indicating mechanism of the pistol according to the preferred to embodiment of the invention.

FIG. 4 is a front view of the barrel clip which secures the body of the syringe to the barrel end of the pistol.

FIG. 5 illustrates the full length hand trigger of the pressure indicating pistol.

FIG. 6 shows in solid lines the ratchet catch arm, and in broken lines the ratchet shaft advancement arm.

FIG. 7 is a isometric view of the rocker arm of the ratchet assembly.

FIGS. 8-12 are partial sectional views of various parts of the invention taken along the corresponding sections lines of FIG. 2.

DETAILED DESCRIPTION OF THE PREFERRED EMBODIMENT

Turning now to the drawings, there is shown in FIGS. 1 and 2 thereof the general aspects of the invention. According to the preferred embodiment the invention includes a frame 10 which includes a barrel 12 and a handle 14 by which the pistol is gripped.

Shown in FIG. 2 in broken lines is a hypodermic-type disposable syringe 16 including a syringe body 18 removably attached to the pistol barrel 12, and a syringe plunger 20 which is removably attached to a slotted bracket 22. For effecting movement of the syringe plunger 20 there is provided a trigger 24 coupled to a ratcheting mechanism, generally designated 26, which in turn engages a ratchet shaft 28 and forces the syringe plunger 20 into the syringe body 18 and injects fluid into a balloon catheter (not shown). Shown in FIGS. 2 and 10 is a ratchet release button 30 for releasing the engagement of the ratchet mechanism 26 from the ratchet shaft 28.

FIGS. 2 and 3 illustrate the pressure indicating mechanism which provides a visual indication of the amount of pressure within the balloon catheter. It should be understood that the cannula of the syringe 16 is connected to the balloon catheter in a conventional manner. The syringe 16 is mounted to the medical pistol by first, pushing the ratchet shaft 28 by its knob 32 in a forward direction until the slotted bracket 22 extends beyond the end of the barrel 12. Because the bracket 22 is horizontally slotted the syringe plunger rim 34 is inserted sideways into the slot of bracket 22, and then the ratchet release button 30 is depressed so that the ratchet shaft 28 and attached syringe plunger 20 can be drawn into the barrel 22 of the pistol. The syringe plunger 20 is drawn into the barrel 12 of the pistol until the syringe body finger tabs 36 are flush against a pistol barrel end flange 38, as shown in FIG. 3. The finger tabs 36 of the syringe body 18 are held in firm engagement with the barrel flange 38 by the use of a slotted clip 40 (FIG. 4).

The clip 40 includes a rounded slot 42 which fits around the body 18 of the syringe, and an internal square grove 44 for clamping the cyringe finger tabs 40 against the square barrel flange 38 when slipped down thereover and into the groove 44. To remove the syringe 16 from the pressure pistol, the syringe body 18 is detached from the pistol barrel 12 by pushing the clip 40 upwardly until it is removed, and then advancing the ratchet shaft 28 forward until the syringe plunger rim 34 can be moved laterally out of the slotted bracket 22. With this arrangement, and these operations, a syringe 16 can be quickly and easily attached or removed from the pressure indicating pistol.

In accordance with one feature, the invention includes a fluid pressure indicator for ascertaining the balloon catheter pressure and thus assure that it is not overinflated and thereby rupture or damage an artery. To that end, the pressure indicating pistol includes a resilient element coupling the ratchet shaft 28 with the syringe plunger 20. In the preferred embodiment of the invention a compression spring 46 is interposed between the ratchet shaft 28 and a coupling shaft 48, the latter of which is attached to the slotted bracket 22. In conjunction with the compression spring 46 there is provided a pressure scale or notch marks 50 and 52 on the coupling shaft 48 for presenting a visual indication of the fluid pressure within the balloon catheter. The coupling shaft 48 slides within a central bore 53 of a chamber end cap 54, and it is the distance between the gauge marks 50, 52 and the end cap 54 which indicates the existing pressure within the balloon catheter.

The compression characteristics of the spring 46 are selected such that when a gauge mark 50 or 52 is about to enter the end cap bore 53, it is known that a predetermined pressure exists in the balloon catheter. For example, a balloon catheter for use in treating plac deposits in arteries is typically inflated to sixty pounds per square inch (PSI). In this instance, the compression spring 46 is selected for a compressibility such that during the catheter inflating procedure a sixty PSI balloon pressure will cause the coupling shaft 48 to be forced into the spring chamber 56 and against the spring force until gauge mark 50 starts entering the chamber cap bore 53. Other gauge marks, such as mark 52 are similarily calibrated to provide a visual indication of greater balloon catheter fluid pressures.

In the preferred form, pressure mark 50 is a band colored yellow and is selectively located on the coupling shaft 48 to indicate a balloon pressure of sixty PSI. The mark 52 is a red colored band positioned to indicate a balloon catheter pressure of one hundred fifty PSI. Other colors, marks or visual indicia may be located on the coupling shaft 48 to provide visual indications of other fluid pressures in the balloon catheter.

While it is important to understand that the ratchet shaft 28 incrementally advances to the left (in FIG. 2) in response to ratchet mechanism operations (to be discussed below) it is also important to realize that because of the resilient element 46, such incremental advancements are not coupled directly to the syringe plunger 20. In other words, the ratchet shaft 28 can move with respect to the coupling shaft 48, and indeed does so to provide a sliding guage for visually indicating balloon pressures. The resilient element 46, in the preferred form of the invention, is comprised of a compression spring 46 which resiliently couples the ratchet shaft 28 to the coupling shaft 48. The inner end 58 of the ratchet shaft 28 includes a chamber 56 for containing the compression spring 46. One end of the coupling shaft 48 includes a piston 60 which slides within the spring chamber 56 and against the compressive force of the spring 46. As noted before, the ratchet shaft inner end 58 includes cap 54 which is threadably engagable with the ratchet shaft 28 and provides a bearing surface through which the coupling shaft 48 slidably moves.

With this arrangement, the incremental forward movements of the ratchet shaft 28 are translated by the compression spring 46 into forward syringe plunger 20, movements which plunger movements, because of the compression spring coupling, are generally inversely proportional to balloon catheter fluid pressures.

FIG. 3 illustrates the situation where the compression spring 46 has experienced on one end thereof the advancing force of the ratchet shaft 28, and on the other end thereof the catheter balloon pressure buildup. In this illustrated instance the balloon has been inflated with fluid such that the back pressure has caused the coupling shaft 48 to compress the spring 46 to the extent that the sixty pound mark 50 is about to enter the chamber cap bore 53 and thus present a visual indication of the balloon catheter pressure.

For use in medical-surgical environments the ratchet shaft 28, chamber end cap 54, compression spring 46, the coupling shaft 48 and ratchet mechanism 26 are constructed of stainless steel. The slotted bracket 22, as well as the gun frame 10, are constructed of a durable plastic. As seen from FIG. 10 of the drawings, the cross-sectional shape of the ratchet shaft 28 is generally round, with ratchet teeth 62 on the bottom, and a flattened top surface 64 which slidable engages with a gun frame upper support 66 to thereby prevent rotation of the ratchet shaft. The ratchet shaft 28 is supported on its bottom surface by the gun frame support 68 (FIG. 2).

The ratchet mechanism 26 is operated by successive trigger movements to produce corresponding reciprocating movements of a ratchet arm 70. The arm 70 engages and pushes on the teeth 62 of the ratchet shaft 28 when reciprocated in the forward direction, and slides backwardly over the inclined part of the teeth 62 when reciprocated backwardly. A ratchet catch arm 72 is biased into engagement with the ratchet teeth 62 to prevent the backward movement of the ratchet arm 70. The catch arm 72 is similar in construction to the ratchet arm 70 except for the longer arm length of the latter. The catch arm 72 pivots about a pin 74 fixed to the frame 10. A hair pin spring 76 is also mounted about pin 74 and has ends tortionally compressible between stop pin 78 and the catch arm 72 underside so as to bias the catch arm upwardly into engagement with the ratchet teeth 62. The ratchet teeth 62 are angled backwardly and the catch arm 72 is angled forwardly so that the catch arm 72 allows forward movement of the ratchet shaft 28, but prevents backward movement thereof. The ratchet arm 70 is similarly pivotal about a floating pin 80 (FIG. 11) and is biased upwardly by a hair pin spring 82, also coiled around pin 80. The two ends of hair pin spring 82 are maintained in torsional compression between the underside of the ratchet arm 70 and fixed pin 85 about which the ratchet rocker arm 84 pivots.

Floating pin 80 is not mounted to the pistol frame 14, but rather provides a pivotal mount for the ratchet arm 70. A dogleg-shaped rocker arm 84, (FIG. 7) pivots about pin 86 which in turn is mounted to both halves of the handle frame 14. In this manner the ratchet arm 70 is rotatable around pin 80, as well as moveable in an arch in response to the pivotal motion of the rocker arm 84 about its stationary pin 86. It can be seen then that the counterclockwise pivotal movement of the rocker arm 84 causes the ratchet arm 70 to arcuately move forwardly to the left in FIG. 2, and engage the ratchet teeth and advance the ratchet shaft.

The full length trigger 24 is constructed of a durable platic and includes a tub 88 which engages with a cam surface 90 of the rocker arm when the trigger 24 is squeezed with the handle. This causes counterclockwise pivotal rocker arm movement which advances the ratchet shaft 28 and thus the syringe plunger 20, as described above. A trigger return spring 92 is maintained at its one end in engagement with the rocker arm 84 by pin 94, and at the other end the spring is captured in a boxed depression 96. Upon release of the trigger 24 the spring 92 expands and rocks the rocker arm 84 clockwise to return the trigger 24 to its initial position and to allow the ratchet arm 70 to engage another tooth 62. As noted above, the ratchet shaft 28 is prevented from following the ratchet arm 70 backwardly by the catch arm 72 which remains engaged while the ratchet arm 70 moves rearwardly.

As noted in FIG. 5 of the drawings the full length trigger 24 includes an elongate finger engaging portion 98 which protrudes through a corresponding elongate slot 100 in the pistol handle, and includes a pair of elongate side flanges 102 which abut with the inner surfaces of the pistol handle 14 adjacent the elongate trigger opening 100 and thereby restrict the outwardly movement of the trigger 24.

The trigger finger engaging portion 98 includes sculptured individual finger grips 101 for accommodating each of the four fingers. When inflating a balloon catheter to one hundred and fifty pounds PSI the finger grips 101 permit the user to drop down on the trigger with the stonger fingers to gain additional mechanical advantage, without the chance of slipping off the trigger while squeezing it. At one end of the trigger 24 there are formed a pair of ears 104 with corresponding outwardy directed pivot pins 106 insertable into respective pistol frame handle bushings 108 (FIG. 12). During assembly, registration of the trigger pivot pins 106 into their respective bushings 108 is assured by the corresponding registratin of frame handle pins 114 into their respective mating sockets. The various sockets, as well as corresponding pins 114, located around the handle valves 14a and 14b are formed in busses 116.

In accordance with one aspect of the invention the stub 88 is positioned on the backside of the trigger 24 at a location near the pivotal end thereof. This is advantageous in gaining additional mechanical leverage to supply the force required to repeatedly ratchet the ratchet shaft 28 forwardly. While more force could be gained by locating the stub 88 even closer to the pivotal end of the trigger 24, the amount by which the rocker arm 84 is rocked is correspondingly reduced. Therefore, it has been found that a good compromise between the force exerted on the rocker arm 84, and the amount by which it is rocked is reached when the stub 88 is placed adjacent the middle finger position as shown in FIG. 2. With this arrangement, the force required to inflate a balloon catheter to one hundred fifty pounds per square inch can be quickly and easily accomplished.

In initially discharging fluid into the balloon catheter the ratchet shaft 28 can be manually advanced by pushing on the knob 32, rather than ratcheting the shaft 28 forward by the trigger 24. As a further aid in rapidly advancing the ratchet shaft 28 there is provided a pair of finger lugs 118 (FIG. 1), one of each located on a side of the figure and near the rear of the pistol top. The user of the medical pistol may use these lugs 118 as index and middle finger anchor points while pushing on the knob 32 with the thumb of that hand, much like using a syringe. Aside from affording a means for quickly advancing the ratchet shaft 28, the finger lugs 118 also allow the user to very carefully control the discharge of the syringe liquid into the balloon catheter with one hand, rather than two hands—one hand on the pistol handle and the other on the push knob 32.

It should be recognized that the muscle motor control of leveraging movements between the fingers and thumb of one hand are much more controllable than the leveraging actions between two hands. Therefore, the user can yet use one hand for steadying the pressure indicating pistol, and the other hand to either quickly initially advance the ratchet shaft 28 by pushing on the knob 32, or precisely control its advancement by using the thumb on the push knob 32 and two fingers on the lugs 118. Indeed, the pressure pistol may even be operated using both the trigger 24 along with the push knob 32 to advance the ratchet shaft 28.

If, for any reason it is desired that the ratchet mechanism 26 be disengaged from the ratchet shaft 28 the release button 30 need merely be pressed. The release button 30 is located at the top rear of the pistol and is easily accessible with the index finger, while the middle finger on a lug 118 and the thumb on the knob 32 is yet effective to control either the advancement or the retarding of the ratchet shaft 28. In other words, the release button 30 can be depressed and maintained in that position while that same hand is still able to control the bi-directional movement of the ratchet shaft 28.

As noted from FIG. 10 of the drawings, the release button 30 includes a hollowed tunnel portion 120 on its underside for straddling the ratchet shaft 28. The two downwardly disposed legs 122 forming the tunnel sides engage the tops of both the catch arm 72 and ratchet arm 70 so that the downward movement of the release button 30 effects a disengagement of the respective arms from the ratchet teeth 62. The depression of the release button 30 thus disengages the arms 70 and 72 from the teeth 62 and permits the ratchet shaft 28 to be slidably moved in either a forward or backward direction. Because the ratchet arm 70 and catch arm 72 are biased upwardly by respective hair pin springs 82 and 76, the release of button 30 automatically engages both such arms back into the ratchet teeth 62. It can be seen from FIG. 10 that the tunnel portion 120 of the release button 30 has a verical distance for allowing the button to move downwardly over the ratchet shaft 28 so as to sufficiently spring the arms 70 and 72 out of engagement with the ratchet teeth 62.

As noted generally in the drawings, the frame 10 of the pressure indicating pistol is constructed in two halves 14a and 14b (FIG. 1) and fasten together at various points by screws. Particularly, FIGS. 2 and 8 illustrate that the end of the barrel 12 includes an alignment pin 124 at the top of the barrel end, and a screw 128 at the bottom for fastening the barrel halves together. At the base of the barrel 12 near the handle another screw 130 is employed to secure the pistol frame halves together. The handle of the pressure indicating pistol is clamped together by screws 132, 134 and 136. As seen from FIG. 2, various other registration pins and matching sockets are located around the edges of the frame halves for ease in assembling the halves together, as well as to provide a solid and sturdy unit when fully assembled.

The handle of the pressure regulating pistol includes on its upper back side a protrusion 140 for maintaining the user's hand on the mid and lower portions of the handle to prevent accidental contact of one's hand with the ratchet teeth 62. As noted in FIG. 1, the upper portion of the barrel is open for viewing the pressure gauge scale marks 50 and 52. In addition, the pistol barrel 12 is constructed of a transparent durable plastic to allow the user to view the position of the pressure gauge marks 50 and 52 through the side of the barrel. Because it is not necessary to view the ratcheting mechanism 26 the inside surfaces of the frame handle 14 are frosted to produce an opaque or translucent effect.

From the foregoing it is seen that the described pressure indicating pistol provides a means for visually ascertaining the pressure buildup resulting from the discharge of liquid from the syringe into an expandable bulb connected to the pistol. Also provided is a highly leveraged ratcheting mechanism and an overriding release which allows the ratchet shaft to move freely in either axial direction. Moreover, the provision of finger lugs closely located to the release button provides the user with the ability to manually advance the ratchet shaft with one hand, or the ability to maintain control of the advancement or retraction of the ratchet shaft while the release button is pushed.

Although the invention has been described above with a certain degree of particularity with the respect to the apparatus involved, it should be understood that the disclosure has been made by way of example only. Consequently, numerous changes in the details and construction of the pressure-indicating pistol may be apparent to those familiar with the art and may be resorted to without departing from the scope of the invention as claimed.

We claim:

1. A pressure indicating injection device for use with a syringe having a body for holding fluid, a discharge outlet and a plunger adapted for discharging fluid from said syringe body into a balloon-type catheter, said device comprising:

a generally pistol-shaped frame having a hand-grip portion, and a barrel-like portion for holding the syringe, including attachment means for removably attaching the syringe body, and bracket means slidably arranged within said barrel-like portion and being attachable to said plunger at one side thereof whereby to facilitate axially advancing said plunger;

advancing means coupled to said bracket means and capable of axially urging said bracket means to thereby advance said plunger and discharge fluid through said discharge outlet, said advancing means including: a coupling shaft at a second side of said bracket means wherein forward movement toward said attachment means urges the plunger of said syringe forwardly to thereby effect a discharge of fluid from said syringe into said catheter; said coupling shaft meeting a resilient element at an end thereof opposite said bracket means; a ratchet shaft arranged with said barrel-like portion generally co-axially with said coupling shaft and having an end cylinder chamger for holding said resilient element and into which said coupling shaft is disposed so as to meet and thereby compress said resilient element upon forward advancement thereof, said ratchet shaft having ratchet teeth generally along one side thereof; the ratchet shaft being incrementally movable by means of a reciprocating ratchet arm, the ratchet arm being actuated by a spring biased trigger, the trigger being arranged with the hand grip portion of the frame whereby to be capable of being squeezed by the user's hand and provide mechanical advantage facilitating the advancement of the plunger against increasing pressure, and a ratcht shaft catch arm preventing back sliding of the ratchet shaft intermediate incremental advances caused by the ratchet arm; and pressure indicating means associated with said advancing means and being responsive to the increasing resistance of advancement of said syringe plunger as fluid discharges into said catheter and indicating the back pressure thereof.

2. The pressure indicating injection device of claim 1 wherein said pressure indicating means includes a resilient element of selected compression characteristics arranged generally between said plunger and said advancing means.

3. The pressure indicating injection device of claim2 wherein said resilient element comprises a compression spring.

4. The pressure indicating injection device of claim 3 wherein said ratchet shaft of said advancing means includes a chamber, said compression spring residing within said chamber and wherein a coupling shaft means extends from said bracket means to resiliently contact said compression spring and thereby providing the coupling of said advancing means to said bracket means.

5. The pressure indicating injection device of claim 1 wherein for use with a syringe of the type having finger lobe means attached to the body of the syringe, said attachment means including a flange against which said finger lobe means are abutted, and a clip for clamping said finger lobe means to said flange.

6. The pressure indicating injection device of claim 1 wherein said bracket means is advanceable outwardly of the end of the barrel-like portion of the frame to effect attachment thereto of said syringe plunger, and wherein said device includes ratchet release means for release of the ratchet arm and catch arm and thereby facilitating retracting said bracket means and the attached plunger into the barrel-like portion.

7. A pressure indicating injection gun for use with a plunger-actuated syringe for injecting fluid contained within a body portion of said syringe into an expandable catheter bulb, or the like, comprising:

a pistol-shaped frame having hand grip and barrel-like portions;

attachment means at said barrel-like portion for removably holding the body of said syringe firmly to said gun frame;

slidable bracket means arranged with said barrel-like portion for removably attaching the plunger of said syringe at one side thereof in movable relation relative to said gun frame, and including a coupling shaft at the opposite side wherein forward movement toward said attachment means urges the plunger of said syringe forwardly to thereby effect a discharge of fluid from said syringe into said bulb;

said coupling shaft meeting a resilient element at an end thereof opposite said bracket means;

a ratchet shaft arranged with said barrel-like portion generally co-axially with said coupling shaft and having an end cylinder chamber for holding said resilient element and into which said coupling shelf is disposed so as to meet and thereby compress said resilient element upon forward advancement thereof, said ratchet shaft having ratchet teeth generally along the bottom side thereof;

a hand actuated ratchet mechanism engagable with said ratchet teeth for advancing said ratchet shaft in a forward direction in discrete forward movements said ratchet mechanism including a finger operated trigger arranged with the hand grip portion of said frame;

pressure indicating scale marks on said coupling shaft at calibrated locations determined by the compression characteristics of said resilient element;

whereby said resilient element translates the discrete forward movement of said ratchet shaft into a resultant coupling shaft and plunger shaft movement which plunger movement is dependent upon fluid pressure in said bulb, said pressure being indicated by the position of the scale marks on said coupling shaft.

8. The pressure indicating injection gun of claim 7 further including a finger lug on each side of said gun frame, and wherein said ratchet shaft further includes an outer end extending externally of said gun frame for use in conjunction with said finger lugs to facilitate a manual push movement of said ratchet shaft in a forward direction.

9. The pressure indicating injection gun of claim 7 further including release means for releasing the engagement of said ratchet mechanism from the teeth of said ratchet shaft so that said ratchet shaft can be moved in a backward direction.

10. The pressure indicating injection gun of claim 7 wherein said ratchet mechanism includes a catch means engageable with said ratchet teeth for preventing backward movement of said ratchet shaft during ratcheting operations.

11. The pressure indicating injection gun of claim 10 further including release means for releasing the engagement of the ratchet mechanism including said catch means from the teeth of said ratchet shaft so that the ratchet shaft can be moved in a backward direction.

12. The pressure indicating injection device of claim 1 wherein said trigger is provided with generally sculptured individual finger grips for accommodating each of the user's four fingers during trigger-squeezing whereby the user may drop down on the trigger with the stronger fingers to gain additional mechanical leverage advantage and wherein said finger grips aid in preventing the fingers from slipping off the trigger during squeezing.

13. The pressure indicating injection gun of claim 7 wherein said trigger is provided with generally sculptured individual finger grips for accommodating each of the user's four fingers during trigger-squeezing whereby the user may drop down on the trigger with the stronger fingers to gain additional mechanical leverage advantage and wherein said finger grips aid in preventing the fingers from slipping off the trigger during squeezing.

* * * * *